United States Patent
Eslahi et al.

(10) Patent No.: US 11,260,149 B2
(45) Date of Patent: Mar. 1, 2022

(54) HYDROGEL FOR CARTILAGE TISSUE REGENERATION

(71) Applicants: Niloofar Eslahi, Tehran (IR); Abdolreza Simchi, Tehran (IR)

(72) Inventors: Niloofar Eslahi, Tehran (IR); Abdolreza Simchi, Tehran (IR)

(*) Notice: Subject to any disclaimer, the term of this patent is extended or adjusted under 35 U.S.C. 154(b) by 59 days.

(21) Appl. No.: 15/935,014

(22) Filed: Mar. 25, 2018

(65) Prior Publication Data

US 2018/0207319 A1 Jul. 26, 2018

Related U.S. Application Data

(60) Provisional application No. 62/512,018, filed on May 28, 2017.

(51) Int. Cl.
| | |
|---|---|
| *A61L 27/52* | (2006.01) |
| *A61L 27/14* | (2006.01) |
| *A61L 27/56* | (2006.01) |
| *A61L 27/44* | (2006.01) |
| *A61L 27/42* | (2006.01) |

(52) U.S. Cl.
CPC ......... *A61L 27/52* (2013.01); *A61L 27/14* (2013.01); *A61L 27/425* (2013.01); *A61L 27/443* (2013.01); *A61L 27/446* (2013.01); *A61L 27/56* (2013.01); *A61L 2400/06* (2013.01); *A61L 2430/06* (2013.01)

(58) Field of Classification Search
CPC combination set(s) only.
See application file for complete search history.

(56) References Cited

PUBLICATIONS

Eslahi et al.; "Hybrid cross-linked hydrogels based on fibrous protein/block copolymers and layered silicate nanoparticles: tunable thermosensitivity, biodegradability and mechanical durability"; Jun. 22, 2016; RSC Adv.; 6: 62944-62957; DOI: 10.1039/c6ra08563f (Year: 2016).*

Liu et al.; "Versatile injectable supramolecular hydrogels containing drug loaded micelles for delivery of various drugs" 2014; Polym. Chem. 5: 1072-1081; DOI: 10.1039/c3py01083j (Year: 2014).*

Niloofar Eslahi. et al. Hybrid cross-linked hydrogels based on fibrous protein/block copolymers and layered silicate nanoparticles: tunable thermosensitivity, biodegradability and mechanical durability, The Royal Society of Chemistry, 2016, issue 67, vol. 6, pp. 62944-62957.

* cited by examiner

*Primary Examiner* — Timothy P Thomas
(74) *Attorney, Agent, or Firm* — Bajwa IP Law Firm; Haris Zaheer Bajwa

(57) ABSTRACT

A method for cartilage tissue engineering including fabricating a nanocomposite, injecting the nanocomposite into a defect site of cartilage, and forming a hydrogel in the defect site of the cartilage using a sol-gel transition responsive to increasing temperature of the nanocomposite from room temperature to 37° C. Fabricating a nanocomposite includes forming an activated copolymer by functionalizing a copolymer, forming a conjugated copolymer by grafting the activated copolymer to a polysaccharide, forming a protein-conjugated copolymer by crosslinking a protein with the conjugated copolymer, forming the nanocomposite by adding a plurality of nanoparticles to the protein-conjugated copolymer.

8 Claims, 15 Drawing Sheets

HYDROGEL FOR CARTILAGE TISSUE REGENERATION

CROSS-REFERENCE TO RELATED APPLICATION

This application claims the benefit of priority from U.S. Provisional Patent Application Ser. No. 62/512,018, filed on May 28, 2017, and entitled "SMART INJECTABLE HYDROGELS FOR CARTILAGE TISSUE ENGINEERING AND FABRICATIONS THEREOF," which is incorporated herein by reference in its entirety.

SPONSORSHIP STATEMENT

This application has been sponsored by Iran Patent Center, which does not have any rights in this application.

TECHNICAL FIELD

The present disclosure generally relates to a method for cartilage tissue engineering, particularly to a method for fabricating a hydrogel for cartilage tissue engineering.

BACKGROUND

Articular cartilage is a flexible connective tissue in which chondrocytes are sparsely distributed into a highly organized extracellular matrix (ECM). The cartilage has low self-repair capacity which is attributed to the lack of chondrocyte mobility and the absence of progenitor cells and vascular networks in the ECM. Therefore, any cartilage damage which occurs because of injury, disease, trauma, or tumor continues to be one the most challenging clinical problems in orthopedics.

Various surgical procedures such as autograft and allograft have been used to treat cartilage damage, but each procedure has its own shortcomings. Autograft—the gold standard for cartilage repair suffers from donor site morbidity and restrained availability. On the other hand, allograft has some limitations including delayed vascular penetration and disease transmission. However, tissue engineering approaches are potential alternative methods for cartilage regeneration without limitations of surgical procedures.

Tissue engineering involves the use of a scaffold which acts as a template for tissue regeneration and provides a suitable environment for cellular growth. Among different scaffolds being developed for cartilage tissue engineering, hydrogels are of great interest due to their suitable properties that can mimic the physiochemical and biological properties of the hydrated ECM of cartilage. Nanostructured smart hydrogels with adjustable physicochemical properties have more structural similarity to natural ECM of cartilage and can up-regulate the interactions between cells and materials for faster tissue regeneration.

Therefore, there is a need for stable nanostructured hydrogels with tunable physicochemical properties for cartilage tissue engineering. Moreover, there is a need for tissue engineering scaffolds which may be stable for a longterm basis to support the growth of chondrocytes or other seeding cells.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for cartilage tissue engineering. The exemplary method may include fabricating a nanocomposite, injecting the nanocomposite into a defect site of cartilage, and forming a hydrogel in the defect site of the cartilage. In some exemplary implementations, fabricating the nanocomposite may include forming an activated copolymer by functionalizing a copolymer, forming a conjugated copolymer by grafting the activated copolymer to a polysaccharide, forming a protein-conjugated copolymer by crosslinking a protein with the conjugated copolymer, and forming the nanocomposite by adding a plurality of nanoparticles to the protein-conjugated copolymer.

The above general aspect may include one or more of the following features. In some exemplary implementations, forming the activated copolymer by functionalizing the copolymer may include functionalizing the copolymer by adding one of a carboxyl group, an amine group, a thiol group, an acrylate group, and an isocyanate group to the copolymer. In one or more exemplary embodiments, the copolymer may include one of poloxamer, polyethylene glycol (PEG), N-isopropyl-acrylamide, or combinations thereof.

According to some exemplary implementations, forming the conjugated copolymer by grafting the activated copolymer to the polysaccharide may include forming a first solution by dissolving the activated copolymer in a buffer solution, forming a second solution by adding a coupling agent to the first solution, and forming a third solution by adding a polysaccharide solution to the second solution. In some exemplary embodiments, the coupling agent may include 1-ethyl-3-(3-dimethylaminopropyl) carbodiimide (EDC) and N-hydroxysuccinimide (NHS). In some exemplary embodiments, EDC and NHS may be present in the buffer solution with a molar ratio between about 1:1 and about 1:2.

According to some exemplary embodiments, forming the conjugated copolymer by grafting the activated copolymer to the polysaccharide may include grafting the activated copolymer to the polysaccharide with a weight ratio between about 8:1 and about 12:1. In some exemplary implementations, the polysaccharide may include one of glycosaminoglycan (GAG) and polysaccharides with a terminal amine group.

According to some exemplary implementations, forming the protein-conjugated copolymer by crosslinking the protein with the conjugated copolymer may include forming a mixture by adding the protein to the conjugated copolymer, and adding a crosslinker to the mixture. In some exemplary embodiments, the protein may include one of keratin, collagen, gelatin, fibroin, or combinations thereof. In some exemplary embodiments, forming the mixture by adding the protein to the conjugated copolymer may include adding the protein to the conjugated copolymer with a weight ratio between about 1:8 and about 1:12.

According to some exemplary embodiments, the crosslinker may include genipin, glutaraldehyde, 1-ethyl-3-(3-dimethylaminopropyl) carbodiimide (EDC), or combinations thereof. In some exemplary embodiments, adding the crosslinker to the mixture may include adding a crosslinker solution with a concentration between about 1 mM and about 10 mM to the mixture at a temperature of less than about 10° C.

According to some exemplary embodiments, forming the nanocomposite by adding the plurality of nanoparticles to the protein-conjugated copolymer may include adding the plurality of nanoparticles with a weight percent less than about 6% of the total weight of the nanocomposite. In some exemplary embodiment, the plurality of nanoparticles may include one of the hydroxyapatite nanoparticles, nanoclay particles, carbon-based nanoparticles, or combinations thereof.

In some exemplary implementations, forming the hydrogel in the defect site of the cartilage may include forming the hydrogel in the defect site of the cartilage using a sol-gel transition responsive to increasing temperature of the nanocomposite from room temperature to about 37° C. In some exemplary embodiments, the hydrogel may have a porous structure with a pore size between about 5 μm and about 100 μm. The hydrogel may have a swelling ratio between about 100% and about 250%.

In another general aspect, the present disclosure describes an exemplary method for cartilage tissue engineering. The exemplary method may include fabricating a nanocomposite, injecting the nanocomposite into a defect site of cartilage, and forming a hydrogel in the defect site of the cartilage using a sol-gel transition responsive to increasing temperature of the nanocomposite from room temperature to a temperature about 37° C.

The above general aspect may include one or more of the following features. In some exemplary implementations, fabricating the nanocomposite may include forming an activated poloxamer by functionalizing poloxamer, forming a conjugated poloxamer by grafting the activated poloxamer to chitosan, forming a keratin-conjugated poloxamer by crosslinking keratin with the conjugated poloxamer by using genipin with a concentration between about 1 mM and about 10 mM, and forming the nanocomposite by adding the plurality of nanoparticles with a weight percent less than about 6% of the total weight of the nanocomposite to the keratin-conjugated poloxamer.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown but is to be accorded the widest possible scope consistent with the principles and features disclosed herein.

Hydrogels are three-dimensional networks of hydrophilic polymers with a high capacity of water uptake while being able to maintain their structural integrity because of their crosslinked structure. Injectable hydrogels for tissue engineering may be formed in-situ after injection at the defect site. The injectable nature of these hydrogels provides an attractive feature of facile and homogenous cell distribution within any defect site prior to gelation in good alignment with the surrounding tissue by a simple minimally invasive procedure.

Thermosensitive hydrogels as specific injectable biomaterials may undergo sol-gel transitions upon exposure to the physiological temperature. The advantage of temperature-triggered hydrogels is the ease of fabrication and administration using minimally invasive implantations. Moreover, using nanostructures in the thermosensitive hydrogels may lead to a synergistic improvement in characteristics such as physicochemical characteristics of hydrogels due to the combination of nanoscale properties of nanomaterials with controllable size and shape along with the adjustable physicochemical properties of thermosensitive hydrogels.

Disclosed herein is an exemplary method for fabricating an injectable thermosensitive nanocomposite for cartilage tissue engineering. The injectable thermosensitive nanocomposite may form a hydrogel in a defect site, which may be similar to the natural extracellular matrix (ECM) of cartilage, and stimulate adhesion and spreading of chondrocyte cells. The thermosensitive nanocomposite may include a crosslinked polymeric matrix of a protein and a conjugated copolymer. Furthermore, the plurality of nanoparticles may be present in the thermosensitive nanocomposite for reinforcing the structure of the nanocomposite. In some exemplary implementations, the thermosensitive nanocomposite may be transformed to a hydrogel upon exposure to the physiological temperature in a defect site of the cartilage.

Figure 1A:
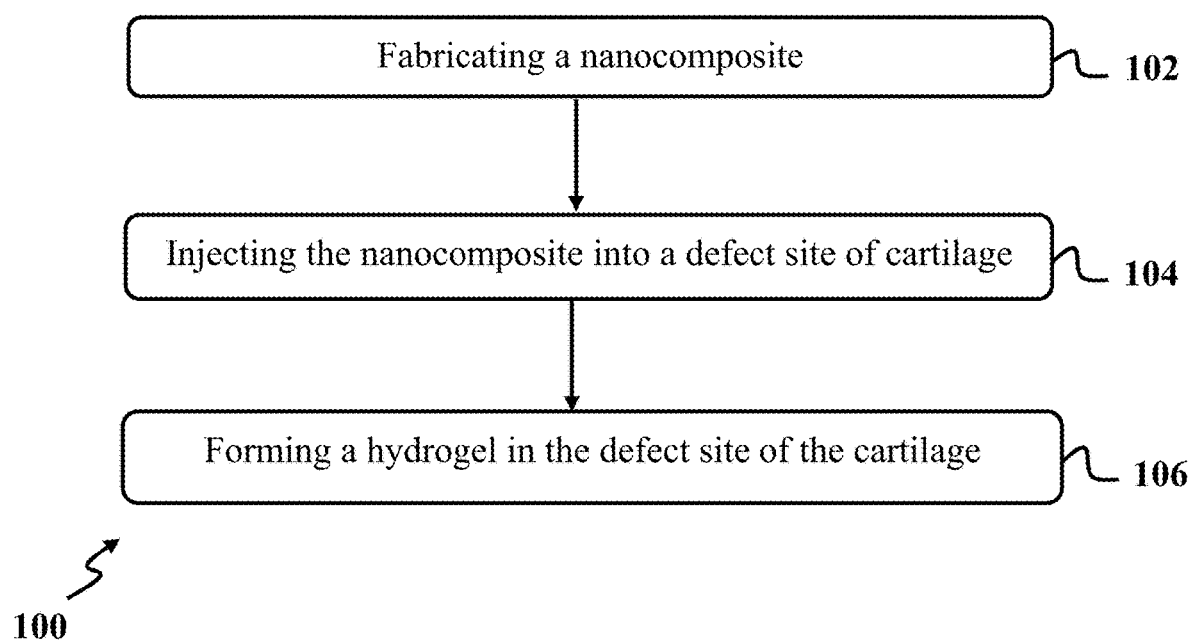
FIG. 1A illustrates a method for cartilage tissue engineering, consistent with one or more exemplary embodiments of the present disclosure.

FIG. 1A is method 100 for cartilage tissue engineering, consistent with one or more exemplary embodiments of the present disclosure. Method 100 may include fabricating a nanocomposite (step 102), injecting the nanocomposite into the defect site of cartilage (step 104), and forming the hydrogel in the defect site of the cartilage (step 106).

Figure 1B:
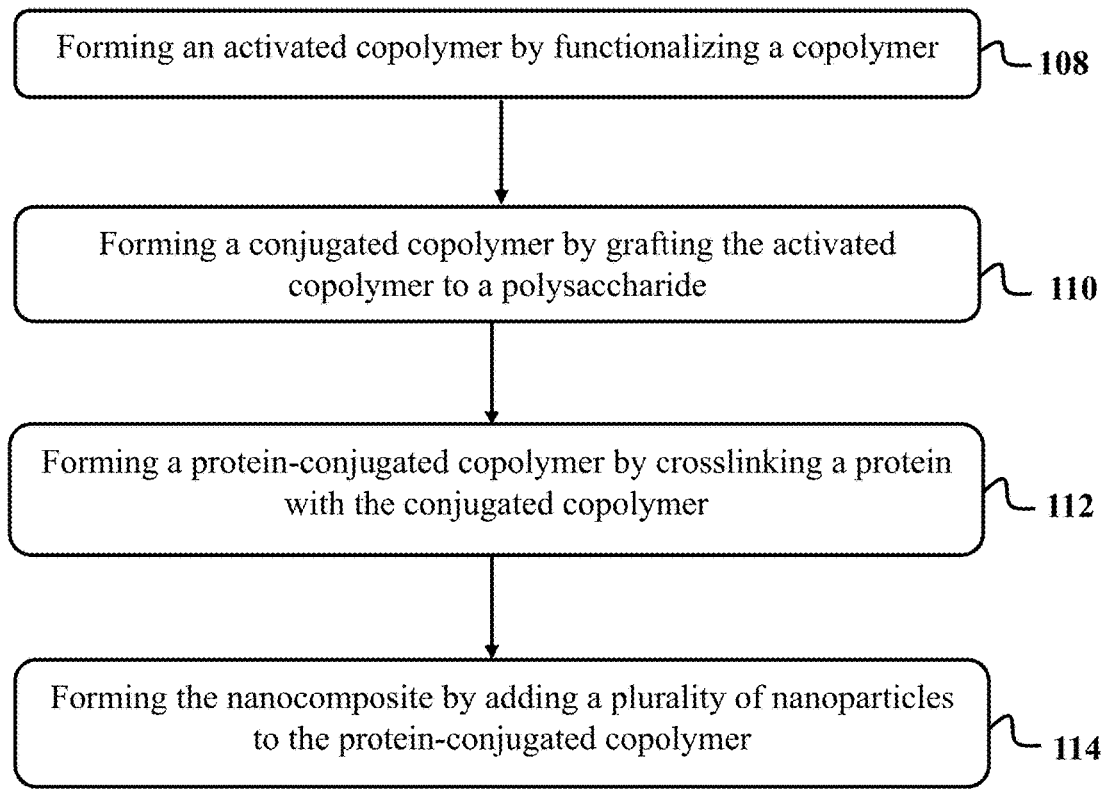
FIG. 1B illustrates a method for fabricating a nanocomposite, consistent with one or more exemplary embodiments of the present disclosure.

FIG. 1B shows an exemplary implementation of step 102 for fabricating the nanocomposite, consistent with one or more exemplary embodiments of the present disclosure. Fabricating the nanocomposite may include forming an activated copolymer by functionalizing a copolymer (step 108), forming a conjugated copolymer by grafting the activated copolymer to a polysaccharide (step 110), forming a protein-conjugated copolymer by crosslinking a protein with the conjugated copolymer (step 112), and forming a nanocomposite by adding a plurality of nanoparticles to the protein-conjugated copolymer (step 114).

Step 108 may include forming the activated copolymer by functionalizing the copolymer. In some exemplary implementations, the copolymer may include one of poloxamer, polyethylene glycol (PEG), N-isopropyl-acrylamide, or combinations thereof. The poloxamer may include one of Pluronic, Tetronic, Synperonic, or combinations thereof. In some exemplary embodiments, forming the activated copolymer by functionalizing the copolymer may include functionalizing the copolymer by adding one of a carboxyl group, an amine group, a thiol group, an acrylate group, and an isocyanate group to the copolymer. In one or more exemplary embodiments, functionalizing the copolymer may include carboxylating the copolymer using succinic anhydride, 4-dimethylaminopyridine, and triethylamine.

Figure 1C:
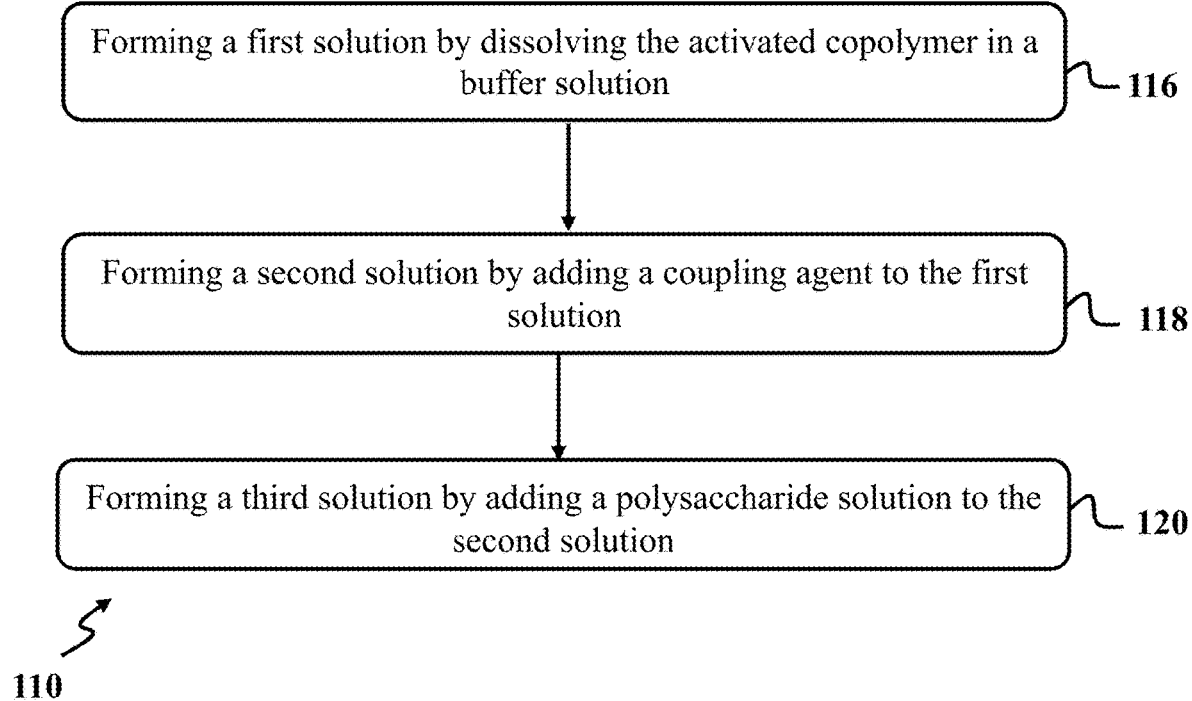
FIG. 1C illustrates a method for forming a conjugated copolymer by grafting the activated copolymer to a polysaccharide, consistent with one or more exemplary embodiments of the present disclosure.

Step 110 may include forming the conjugated copolymer by grafting the activated copolymer to the polysaccharide. FIG. 1C shows an exemplary implementation of step 110 for forming the conjugated copolymer by grafting the activated copolymer to the polysaccharide, consistent with one or more exemplary embodiments of the present disclosure. Forming the conjugated copolymer by grafting the activated copolymer to the polysaccharide may include forming a first solution by dissolving the activated copolymer in a buffer solution (step 116), forming a second solution by adding a coupling agent to the first solution (step 118), and forming a third solution by adding a polysaccharide solution to the second solution (step 120).

Step 116 may include forming the first solution by dissolving the activated copolymer in the buffer solution. Dissolving the activated copolymer in the buffer solution may include adding the activated copolymer in the buffer solution to form the first solution and stirring the first solution at room temperature. In an exemplary embodiment, the buffer solution may include a phosphate buffer solution with a pH level between about 5 and about 5.5.

Step 118 may include forming the second solution by adding the coupling agent to the first solution. In some exemplary embodiments, the coupling agent may include 1-ethyl-3-(3-dimethylaminopropyl) carbodiimide (EDC) and N-hydroxysuccinimide (NHS). In some exemplary embodiments, EDC and NHS may be present in the buffer solution with a molar ratio between about 1:1 and about 1:2.

Step 120 may include forming the third solution by adding the polysaccharide solution to the second solution. In an exemplary embodiment, forming the third solution by adding the polysaccharide solution to the second solution may be followed by stirring the third solution for a time period about 24 hours. In some exemplary implementations, the conjugated copolymer may be formed by grafting the activated copolymer to the polysaccharide upon adding the polysaccharide solution to the second solution. In some exemplary embodiments, the activated copolymer may be grafted to the polysaccharide with a weight ratio between about 8:1 and about 12:1.

In some exemplary implementations, the polysaccharide may include one of glycosaminoglycan (GAG) molecules and polysaccharides with a terminal amine group. The GAG molecules may be used with aminated copolymers and may include one of hyaluronic acid, heparin, chondroitin sulfate, dermatan sulfate, or combinations thereof. The polysaccharides with a terminal amine group may be used with carboxylated copolymers and may include chitosan or chitosan derivatives.

In some exemplary implementations, the conjugated copolymers may be formed through a conjugation process which may be conducted by forming amide bonds between amine groups of the polysaccharides and carboxyl groups of the copolymers using EDC and NHS. In some exemplary embodiments, the conjugated copolymers may be purified in a dialysis process and lyophilized to obtain conjugated copolymers in a powder form.

Step 112 may include forming the protein-conjugated copolymer by crosslinking the protein with the conjugated copolymer. In some exemplary embodiments, forming the protein-conjugated copolymer by crosslinking the protein with the conjugated copolymer may include forming a mixture by adding the protein to the conjugated copolymer, and adding a crosslinker to the mixture.

In some exemplary embodiments, forming the mixture by adding the protein to the conjugated copolymer may include adding a protein to a solution of the conjugated copolymer in phosphate buffered saline (PBS) solution with a pH level of about 7.4. In some exemplary embodiments, adding the protein to the conjugated copolymer may comprise adding with a weight ratio between about 1:8 and about 1:12.

In some exemplary embodiments, the protein may include one of keratin, collagen, gelatin, fibroin, or combinations thereof. In one or more exemplary embodiments, the protein may be low-sulfur α-keratin with a molecular weight between about 40 kDa and about 60 kDa. In some exemplary embodiment, keratin may be extracted from fibrous proteins such as wool, feather, and hair. The extraction of keratin may be done through one of hydrothermal, chemical hydrolysis, reduction, oxidation, sulfitolysis, or enzymatic procedures.

In some exemplary embodiments, adding the crosslinker to the mixture may include adding a crosslinker solution with a concentration between about 1 mM and about 10 mM to the mixture. In some exemplary embodiments, the crosslinker may include one of natural crosslinker, synthetic crosslinker, or combinations thereof. The natural crosslinker may include genipin. The synthetic crosslinker may include glutaraldehyde, 1-ethyl-3-(3-dimethylaminopropyl) carbodiimide (EDC), or combinations thereof. In some exemplary embodiments, genipin may form chemical bonds between primary amine groups of keratin and chitosan with ester groups of genipin in crosslinking reactions.

Step 114 may include forming the nanocomposite by adding the plurality of nanoparticles to the protein-conjugated copolymer. In some exemplary embodiments, the plurality of nanoparticles may be added to the protein-conjugated copolymer with a weight percent less than about 6% of the total weight of the nanocomposite to the protein-conjugated copolymer. In some exemplary embodiments, the plurality of nanoparticles may include one of the hydroxyapatite nanoparticles, nanoclay particles, carbon-based nanoparticles, or combinations thereof.

Referring back to FIG. 1A, step 104 may include injecting the nanocomposite into the defect site of the cartilage. In some exemplary embodiments, the defect site of cartilage may include surfaces of a portion of the musculoskeletal system which may be damaged because of injury, disease, trauma, or tumor. In some exemplary embodiments, the nanocomposite may be administered into the defect site via a minimally invasive injection. Regardless of the size and shape of the defect site, the nanocomposite may fill the defect site because of its low-viscosity feature.

Figure 3:
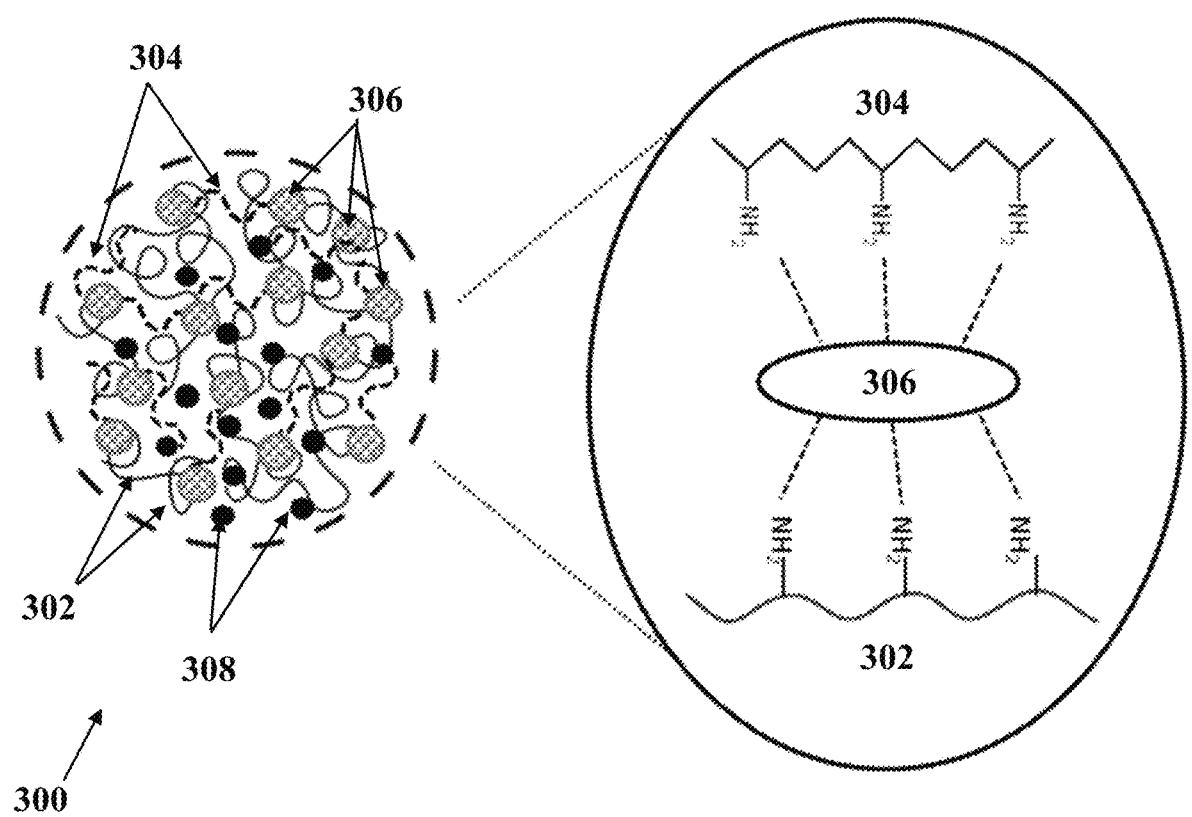
FIG. 3 illustrates a schematic view of an exemplary hydrogel, consistent with one or more exemplary embodiments of the present disclosure.

Step 106 may include forming the hydrogel in the defect site of the cartilage. In some exemplary implementations, forming the hydrogel in the defect site of the cartilage may include forming the hydrogel in the defect site of the cartilage using the sol-gel transition by increasing temperature of the nanocomposite from room temperature to about 37° C. FIG. 3 shows a schematic view of exemplary hydrogel 300 for cartilage tissue engineering, consistent with one or more exemplary embodiments of the present disclosure.

In some exemplary embodiments, hydrogel 300 may include conjugated poloxamer 302, keratin 304, genipin 306, and plurality of silicate nanoparticles 308. In some exemplary embodiments, hydrogel 300 may have a porous structure with a pore size between about 5 μm and about 100 μm. In some exemplary embodiments, hydrogel 300 may have a swelling ratio between about 100% and about 250%.

In one or more exemplary embodiments, the presence of chitosan as the polysaccharide in conjugated poloxamer 302 may enhance stiffness and mechanical strength of hydrogels 300. Chitosan has a similar structure to GAG molecules and may be a promising biomaterial for modulating the morphology of chondrocytes, promoting cellular differentiation, and stimulating cartilage regeneration.

In some exemplary embodiments, keratin 304 may have high biocompatibility and stability properties. Keratin 304 as the fibrous protein may support cellular adhesion, proliferation, and migration due to the presence of peptide motifs in the structure. Therefore, using keratin 304 in hydrogel 300 may mimic hydrogel 300 to the extracellular matrix (ECM) of cartilage and provide a suitable environment for cartilage tissue regeneration. In one or more exemplary embodiments, genipin molecules 306 may form chemical bonds between primary amine groups of conjugated poloxamer 302 and keratin 304 with ester groups of genipin 306 in crosslinking reactions.

In one or more exemplary embodiments, using genipin 306 in hydrogel 300 may have anti-inflammatory, antiphlogistic, neurogenic, and hemostatic effects without any cytotoxicity on hydrogel 300 for tissue engineering applications, for example, cartilage tissue engineering. In some exemplary embodiments, using genipin 306 in hydrogel 300 may form tunable viscoelastic, physical, and biological features in hydrogel 300. Chemical crosslinking by genipin may improve the stability of hydrogel 300. In one or more exemplary embodiments, problems of conjugated poloxamer 302 such as poor stability and low mechanical strength may limit their applications. Therefore, crosslinking the conjugated poloxamer with keratin 304 using genipin 306 may overcome these constraints and improve the stability and mechanical strength of conjugated poloxamer 302 and hydrogel 300.

In some exemplary embodiments, plurality of silicate nanoparticles 308 may be uniformly dispersed within hydrogel 300 for reinforcing and adjusting the mechanical properties of hydrogel 300. In one or more exemplary embodiments, the exfoliated structure of plurality of silicate nanoparticles 308 may act as multifunctional crosslinkers in the structure of hydrogels. While not being bound by any theory, the presence of conjugated poloxamer 302, keratin 304, genipin 306, and plurality of silicate nanoparticles 308 in the structure of hydrogel 300 may have a synergistic effect in fabricating a hydrogel as a suitable scaffold for promoting cartilage tissue regeneration.

Figure 2:
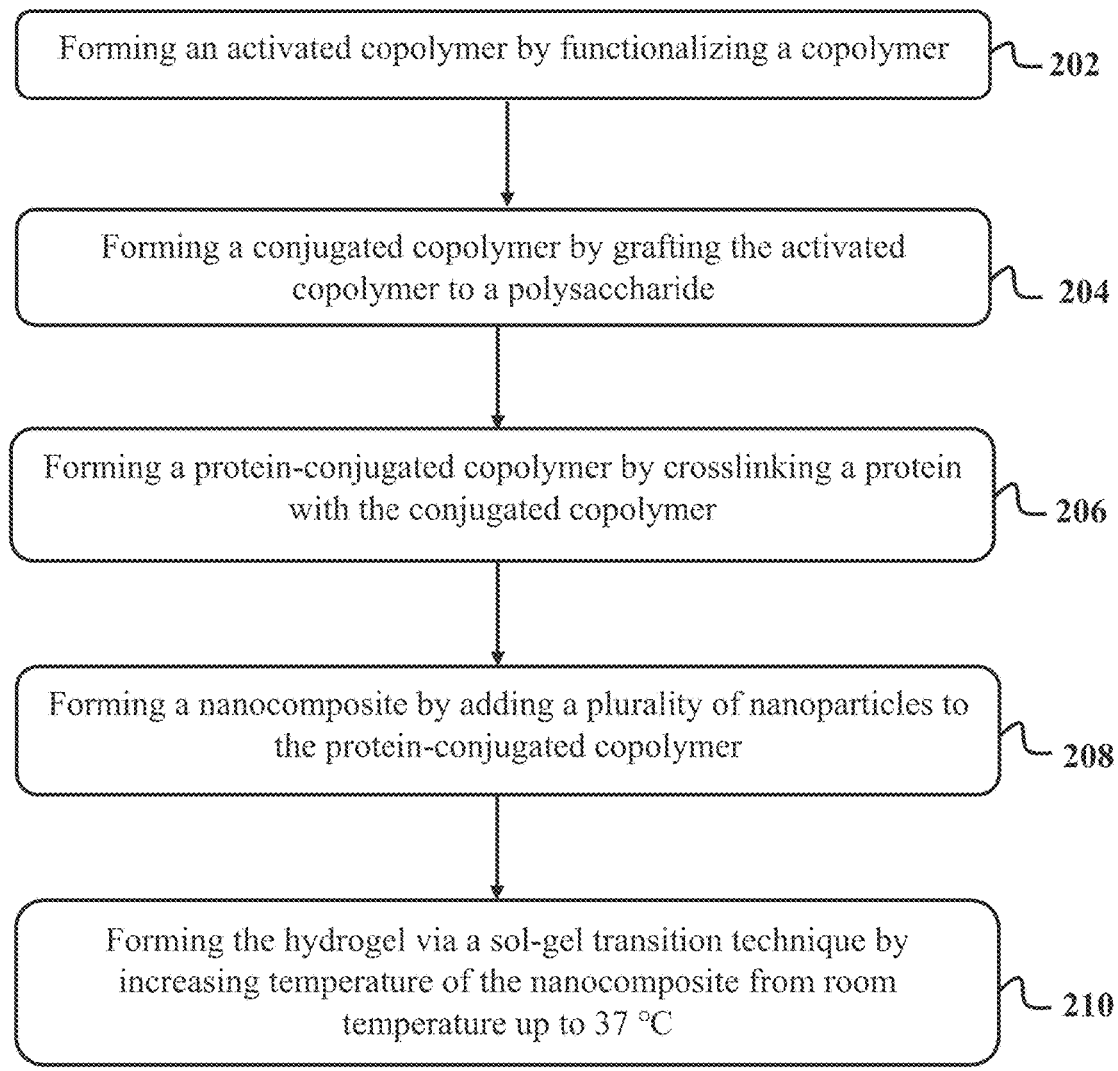
FIG. 2 illustrates a method for fabricating a hydrogel for cartilage tissue engineering, consistent with one or more exemplary embodiments of the present disclosure.

In one or more exemplary embodiments of the present disclosure, a method for fabricating a hydrogel for cartilage tissue engineering is disclosed. FIG. 2 shows an exemplary method 200 for fabricating a hydrogel for cartilage tissue engineering, consistent with one or more exemplary embodiments of the present disclosure. Method 200 may include forming an activated copolymer by functionalizing a copolymer (step 202), forming a conjugated copolymer by grafting the activated copolymer to a polysaccharide (step 204), forming a protein-conjugated copolymer by crosslinking a protein with the conjugated copolymer (step 206), forming a nanocomposite by adding a plurality of nanoparticles to the protein-conjugated copolymer (step 208), and forming the hydrogel via a sol-gel transition technique by increasing temperature of the nanocomposite from room temperature up to 37° C. (step 210).

Step 202 may include may include forming the activated copolymer by functionalizing the copolymer. In some exemplary implementations, the copolymer may include one of poloxamer, polyethylene glycol (PEG), N-isopropyl-acrylamide, or combinations thereof. The poloxamer may include one of Pluronic, Tetronic, Synperonic, or combinations thereof. In some exemplary embodiments, forming the activated copolymer by functionalizing the copolymer may include functionalizing the copolymer by adding one of a carboxyl group, an amine group, a thiol group, an acrylate group, and an isocyanate group to the copolymer.

Step 204 may include forming the conjugated copolymer by grafting the activated copolymer to the polysaccharide. In an exemplary implementation, forming the conjugated copolymer by grafting the activated copolymer to the polysaccharide may be similar to step 110 and may be conducted through an exemplary procedure as shown in FIG. 1C. Referring to FIG. 1C, the exemplary procedure may include forming a first solution by dissolving the activated copolymer in a buffer solution (step 116), forming a second solution by adding a coupling agent to the first solution (step 118) and adding a polysaccharide solution to the second solution (step 120).

Step 206 may include forming the protein-conjugated copolymer by crosslinking the protein with the conjugated copolymer. In some exemplary embodiments, forming the protein-conjugated copolymer by crosslinking the protein with the conjugated copolymer may include forming a mixture by adding the protein to the conjugated copolymer, and adding a crosslinker to the mixture.

In some exemplary embodiments, forming the mixture by adding the protein to the conjugated copolymer may include adding a protein to a solution of the conjugated copolymer in phosphate buffered saline (PBS) with a pH level of about 7.4. In some exemplary embodiments, the protein may be added to the conjugated copolymer with a weight ratio between about 1:8 and about 1:12. In some exemplary embodiments, the protein may include one of keratin, collagen, gelatin, fibroin, or combinations thereof. In one or more exemplary embodiments, the protein may be low-sulfur α-keratin with a molecular weight between about 40 kDa and about 60 kDa.

In some exemplary embodiments, adding the crosslinker to the mixture may include adding a crosslinker solution with a concentration between about 1 mM and about 10 mM to the mixture. In some exemplary implementations, the crosslinker may include one of natural crosslinker, synthetic crosslinker, or combinations thereof. The natural crosslinker may include genipin. The synthetic crosslinker may include glutaraldehyde, 1-ethyl-3-(3-dimethylaminopropyl) carbodiimide (EDC), or combinations thereof. In some exemplary embodiments, genipin may form chemical bonds between primary amino groups of keratin and chitosan with ester groups of genipin in crosslinking reactions.

Step 208 may include forming the nanocomposite by adding the plurality of nanoparticles to the protein-conjugated copolymer. In some exemplary embodiments, forming the nanocomposite by adding the plurality of nanoparticles to the protein-conjugated copolymer may include adding the plurality of nanoparticles with a weight percent less than about 6% of the total weight of the nanocomposite to the protein-conjugated copolymer. In some exemplary embodiment, the plurality of nanoparticles may include one of the hydroxyapatite nanoparticles, nanoclay particles, carbon-based nanoparticles, or combinations thereof.

Step 210 may include forming the hydrogel via the sol-gel transition technique by increasing temperature of the nanocomposite from room temperature up to a temperature of about 37° C. In some exemplary implementations, forming the hydrogel via the sol-gel transition technique may include injecting the nanocomposite into a site, for example, into a biological site or into a mold. The biological site may include surfaces of a portion of the musculoskeletal system which may be the defect sites of the cartilage.

EXAMPLES

Example 1: Fabrication of a Nanocomposite for Cartilage Tissue Engineering

In this example, an exemplary hydrogel was fabricated through the steps of fabricating a nanocomposite, injecting the nanocomposite into a defect site of the cartilage, and forming a hydrogel in the defect site of the cartilage. At first, the nanocomposite was fabricated through the steps of forming an activated copolymer by functionalizing a copolymer, forming a conjugated copolymer by grafting the activated copolymer to a polysaccharide, forming a protein-conjugated copolymer by crosslinking a protein with the conjugated copolymer, and forming a nanocomposite by adding a plurality of nanoparticles to the protein-conjugated copolymer.

In order to form the activated copolymer by functionalizing the copolymer, the poloxamer as the copolymer was carboxylated as follows. At first, a plurality of poloxamer with a molecular weight between about 6.5 and about 14 kDa was dissolved in dioxane to form a poloxamer solution with a concentration between about 10% and about 20% of the weight of the poloxamer solution.

After that, succinic anhydride, 4-dimethylaminopyridine (DMAP), and triethylamine (TEA) were added to the poloxamer solution to form a mixture. The concentration of the succinic anhydride was between about 25 mM and about 50 mM in the mixture. The concentration of the DMAP was between about 20 mM and about 40 mM in the mixture, and the concentration of the TEA was between about 20 mM and about 40 mM in the mixture.

After that, the mixture was stirred for a time period between 24 hours and 48 hours for completing the carboxylation of the poloxamer molecules. After carboxylation of the poloxamer molecules, dioxane as the solvent was removed from the mixture by employing a rotary evaporator, and residue of the mixture was filtered and precipitated in cold diethyl ether twice for purification. Also, the precipitate was dried under vacuum overnight to obtain carboxylated poloxamer in a powder form.

In the next step, a conjugated poloxamer was formed by grafting the carboxylated poloxamer to a polysaccharide with a weight ratio about 10:1 through the following steps. At first, a first solution was formed by dissolving the carboxylated poloxamer in a phosphate buffer solution with a pH level about 5. The first solution was stirred at room temperature until the activated copolymer was dissolved completely. Then, a second solution was formed by adding a solution of coupling agents to the first solution. The solution of coupling agents included 1-ethyl-3-(3-dimethylaminopropyl) carbodiimide (EDC) and N-hydroxysuccinimide (NHS) with a molar ratio of about 1:1.

After that, a third solution was formed by adding a chitosan solution as a polysaccharide solution to the second solution dropwise. The third solution was stirred for a time period about 24 hours. The chitosan solution was prepared by dissolving a polysaccharide in a phosphate buffer solution with a pH level of about 5. Therefore, the conjugated poloxamer was formed by grafting the carboxylated poloxamer to the amine groups of chitosan upon adding the chitosan solution to the second solution. Then, the conjugated poloxamer was purified in a dialysis process and lyophilized to obtain conjugated copolymers in a powder form.

In the next step, the protein-conjugated copolymer was formed by crosslinking keratin as the protein with the conjugated poloxamer. At first, keratin was added to the conjugated poloxamer. A mixture with a pH level of about 7.4 was formed by adding keratin to the conjugated poloxamer with a weight ratio of about 1:10.

Keratin was extracted from wool through a sulfitolysis process. In the sulfitolysis process, the reducing agent, such as sodium bisulfate or metabisulfite was used to break down the disulfide bonds along with urea as a denaturing agent to cleave hydrogen bonds in keratin fibers. Also, sodium dodecyl sulfate (SDS) was used not only for accelerating the extraction rate, but also it could act as a stabilizing agent for regenerating keratin. Moreover, the electrophoresis SDS-polyacrylamide gel (SDS-PAGE) test indicated that the extracted keratin was mainly composed of low-sulfur α-keratin with molecular weight between 40-60 kDa.

After that, a genipin solution as a crosslinker with a concentration between about 5 mM and about 10 mM was added to the mixture to form keratin-conjugated poloxamer at a temperature about 10° C. Genipin formed chemical bonds between primary amino groups of the keratin and the chitosan with the ester groups of genipin in crosslinking reactions.

In the next step, the nanocomposite was formed by adding the plurality of silicate nanoparticles to the keratin-conjugated poloxamer. The silicate nanoparticles were Laponite nanoparticle with a weight percent less than about 6% of the total weight of the nanocomposite. The silicate nanoparticles were added to the keratin-conjugated poloxamer for reinforcing the structure of the keratin-conjugated poloxamer.

After fabricating the nanocomposite, the nanocomposite was used for cartilage tissue engineering by injecting the nanocomposite into a defect site of the cartilage. After injecting the nanocomposite into the defect site of the cartilage, the temperature of the nanocomposite was increased from room temperature to the body temperature due to exposure of the nanocomposite to the physiological temperature which is about 37° C. While the nanocomposite was thermosensitive, it was transformed into a hydrogel in a sol-gel transition. Finally, the hydrogel in the defect site provided a suitable environment for migration of chondrocytes and cartilage tissue regeneration.

Example 2: Morphological Characteristics of the Hydrogel

The microstructure of the tissue engineering scaffolds is important for controlling mass transport, aiding the delivery of biological moieties, and regenerating tissues. In this example, the microstructure of an exemplary hydrogel, which was fabricated as described accordingly to exemplary embodiments in the present disclosure, was studied using scanning electron microscopy (SEM).

Figure 4A:
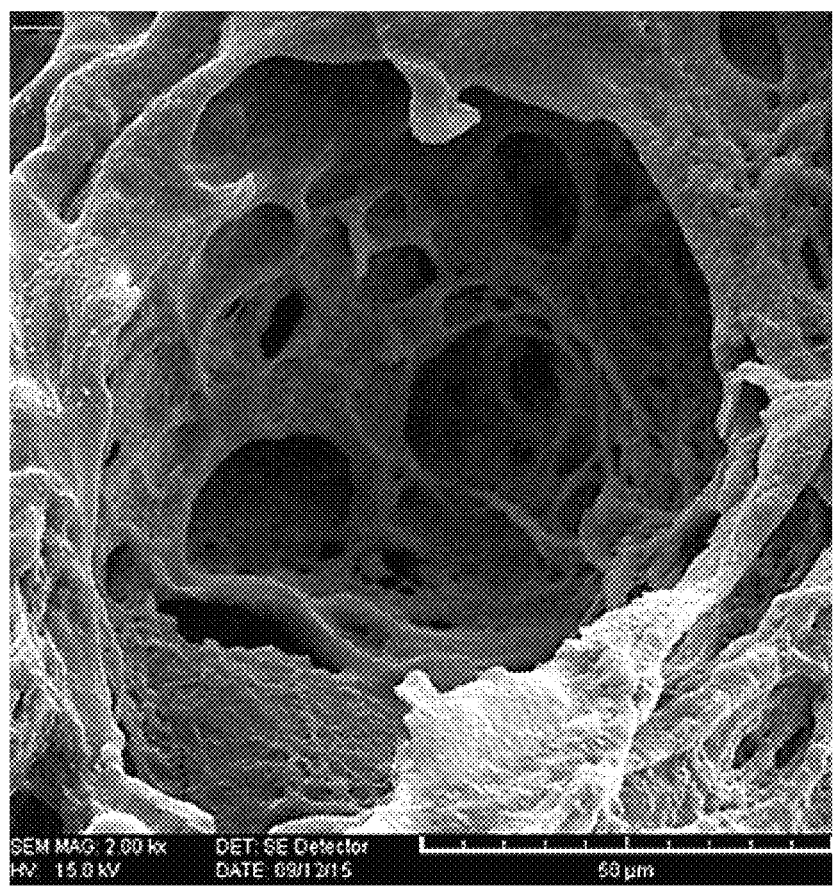
FIG. 4A illustrates a scanning electron microscope (SEM) image of an exemplary hydrogel without genipin, consistent with one or more exemplary embodiments of the present disclosure.
Figure 4B:
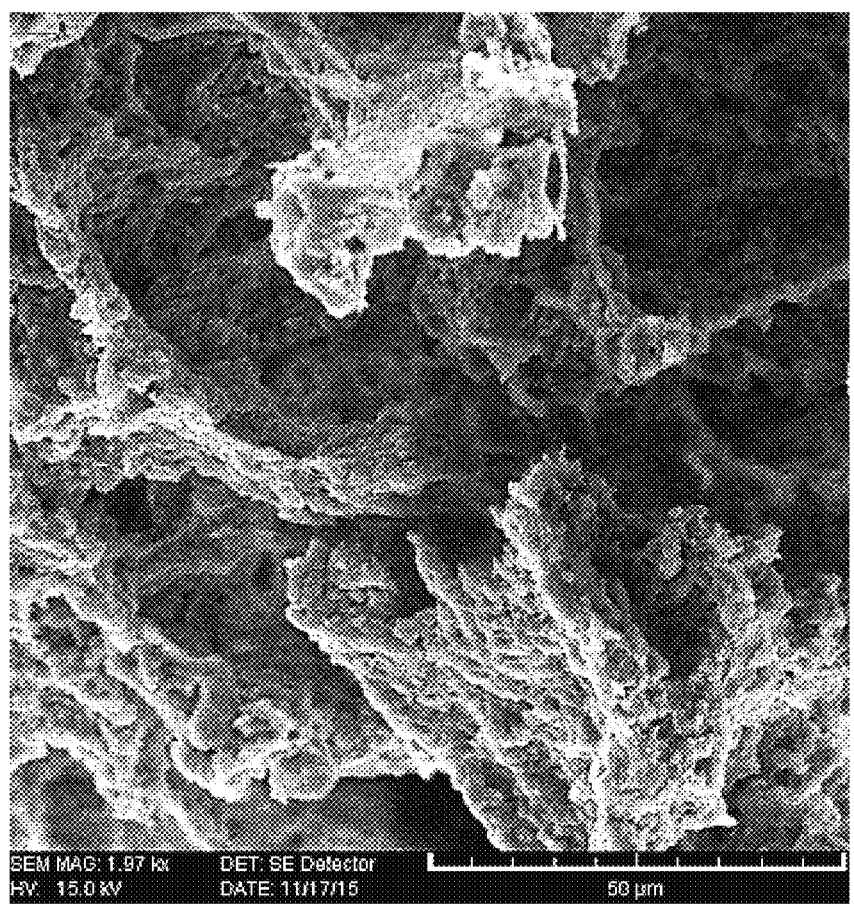
FIG. 4B illustrates an SEM image of an exemplary hydrogel with genipin, consistent with one or more exemplary embodiments of the present disclosure.

FIG. 4A shows a scanning electron microscope (SEM) image of an exemplary hydrogel without genipin, consistent with one or more exemplary embodiments of the present disclosure. FIG. 4B shows an SEM image of an exemplary hydrogel with 10 mM genipin, consistent with one or more exemplary embodiments of the present disclosure. Referring to FIGS. 4A and 4B, the interior microstructures of the exemplary hydrogel show that the addition of genipin as the natural crosslinker leads to a denser structure with smaller pores due to the chemical crosslinking reactions.

Figure 4C:
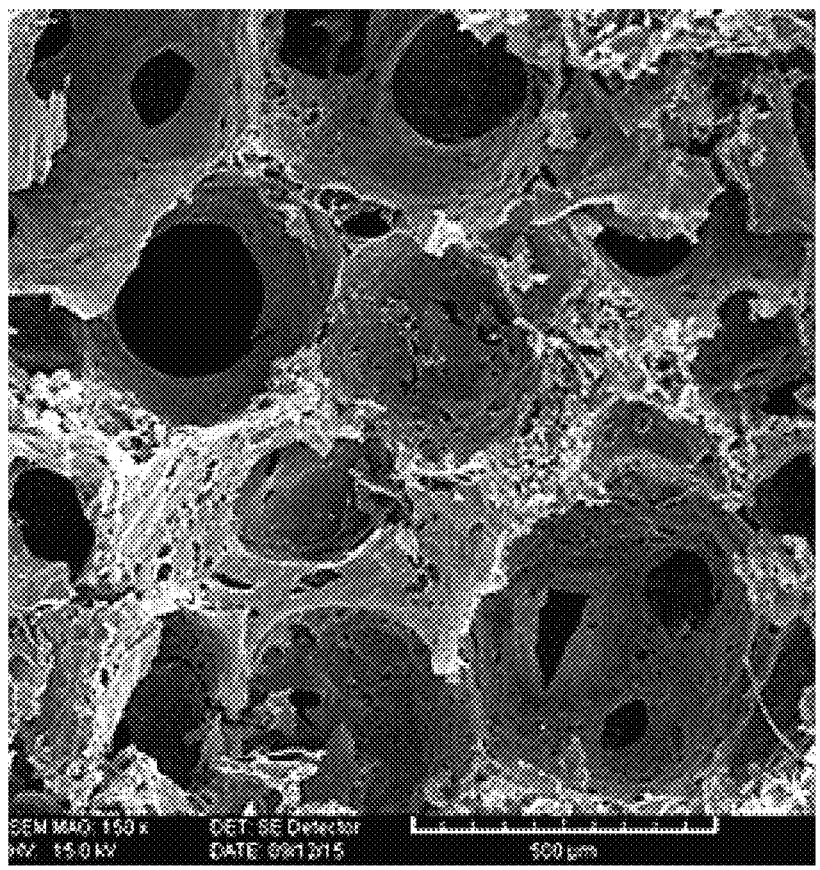
FIG. 4C illustrates an SEM image of an exemplary hydrogel without silicate nanoparticles, consistent with one or more exemplary embodiments of the present disclosure.
Figure 4D:
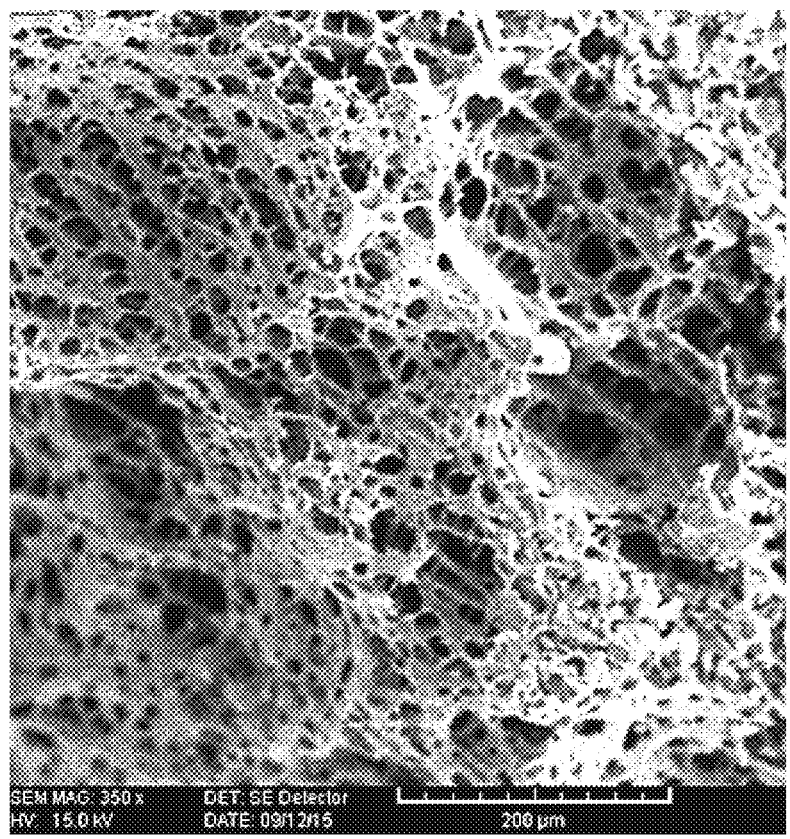
FIG. 4D illustrates an SEM image of an exemplary hydrogel with silicate nanoparticles, consistent with one or more exemplary embodiments of the present disclosure.

FIG. 4C shows an SEM image of an exemplary hydrogel without silicate nanoparticles, consistent with one or more exemplary embodiments of the present disclosure. FIG. 4D shows an SEM image of an exemplary hydrogel with 6% of silicate nanoparticles, consistent with one or more exemplary embodiments of the present disclosure. Referring to FIGS. 4C and 4D, there is a decreasing trend in the pore size by incorporating the silicate nanoparticles into the exemplary hydrogel. There is also no obvious agglomeration of the silicate nanoparticles which indicates good dispersion of silicate nanoparticles in the polymeric matrix of chitosan.

Referring again to FIGS. 4A-4D, the dehydrated cross-sections of the exemplary hydrogels represent the homogeneous and porous structure of the hydrogel which is suitable for cartilage tissue engineering. The pores of the exemplary hydrogel have irregular shapes with a pore size between about 5 μm and about 100 μm. Moreover, the structural integrity of the exemplary hydrogels indicates a good compatibility between components of the exemplary hydrogel.

Example 3: Fourier Transform Infrared Spectroscopy of the Nanocomposite

Figure 5:
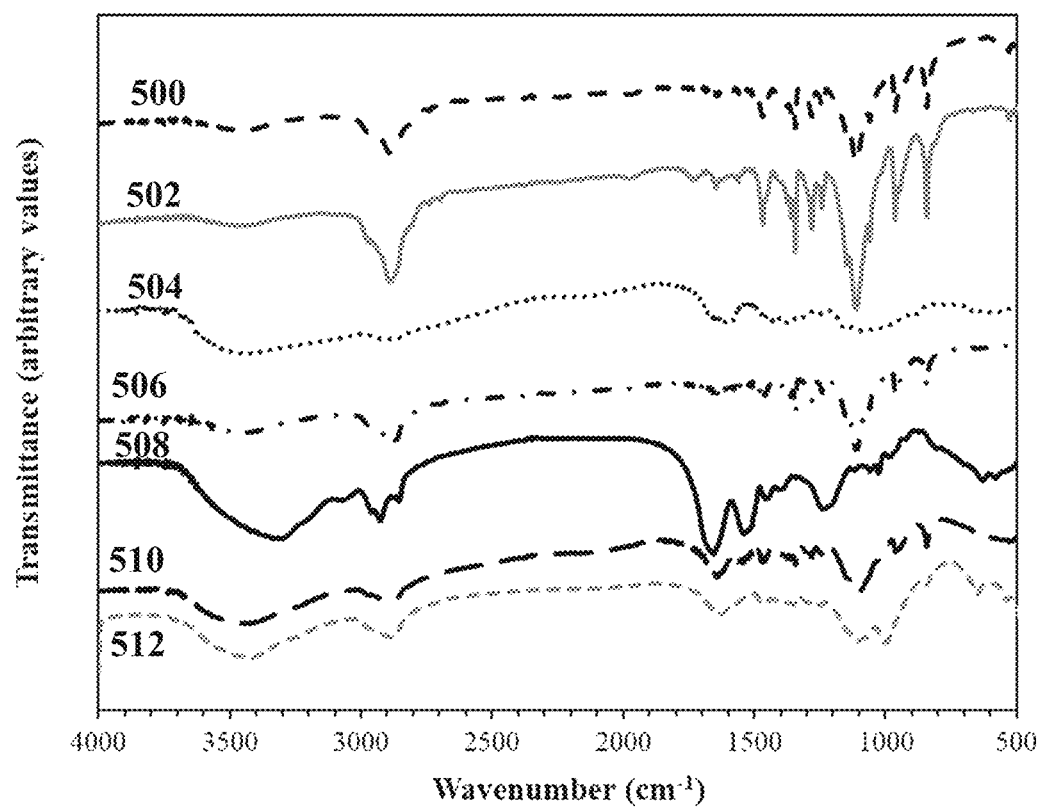
FIG. 5 illustrates Fourier-transform infrared (FT-IR) spectra of an exemplary hydrogel and components thereof, consistent with one or more exemplary embodiments of the present disclosure.

In this example, copolymer functionalization, copolymer conjugation, crosslinking of a protein-conjugated copolymer, and fabricating an exemplary nanocomposite, which was fabricated as described accordingly to exemplary embodiments in the present disclosure, were evaluated by comparing Fourier-transform infrared (FT-IR) spectra of the exemplary nanocomposite and its components. FIG. 5 shows FT-IR spectra of poloxamer 500, carboxylated poloxamer 502, chitosan 504, conjugated poloxamer 506, keratin 508, keratin-conjugated poloxamer 510, and nanocomposite 512 consistent with one or more exemplary embodiments of the present disclosure.

Referring to FIG. 5, the spectra of poloxamer 500 and carboxylated poloxamer 502 show a peak at a wavelength of about 1108 $cm^{-1}$ due to the stretching of aliphatic ether groups, and a peak at a wavelength about 1243 $cm^{-1}$ due to the twisting vibration of $CH_2$ groups in the poloxamer molecules. Also, there is a peak at a wavelength of about 1732 $cm^{-1}$ in the spectrum of activated poloxamer 502 which is assigned to the stretching vibrations of carboxyl (COOH) groups. Therefore, the presence of the peak at a wavelength of about 1732 $cm^{-1}$ confirms the successful carboxylation of the poloxamer molecules.

Referring again to FIG. 5, the wide peak which is appeared in the spectrum of chitosan 504 at a wavelength between about 3100 $cm^{-1}$ and about 3600 $cm^{-1}$ with a maximum intensity at a wavelength about 3448 $cm^{-1}$, is due to overlapping of the stretching vibrations of functional groups engaged in hydrogen bonds such as O—H and N—H. Moreover, the peaks at wavelengths of about 1152, about 1098, and about 1031 $cm^{-1}$ in the spectrum of chitosan 504 correspond to the stretching bands of bridging oxygen (C—O—C) as characteristics of glycosidic linkage in the polysaccharide structure of chitosan.

Referring again to FIG. 5, the spectrum of the conjugated poloxamer 506 exhibits a peak at a wavelength of about 1650 $cm^{-1}$ for the stretching vibration of C=O in the amide bonds which could be formed between the carboxyl groups of carboxylated poloxamer and the amine groups of chitosan. Therefore, it can be concluded that the conjugation of the poloxamer molecules to the chitosan molecules was successful. Besides, the spectrum of the conjugated poloxamer 506 does not show any peak at a wavelength of about 1732 $cm^{-1}$ for the stretching vibrations of carboxyl groups in comparison with the spectrum of carboxylated poloxamer 502. Therefore, the absence of the peak corresponding to the carboxylic groups at a wavelength about 1732 $cm^{-1}$ in the spectrum of conjugated poloxamer 506 also indicates that all functional carboxyl groups of the poloxamer molecules are consumed in the conjugation process of the poloxamer molecules to the chitosan molecules.

Referring again to FIG. 5, the spectrum of keratin 508 shows characteristic absorption bands assigned mainly to the amide bonds at wavelengths between about 1200 $cm^{-1}$ and about 1700 $cm^{-1}$. The peaks of amide I are present at wavelengths between about 1700 $cm^{-1}$ to about 1600 $cm^{-1}$ due to the stretching vibration of the C=O groups. The peaks of amide II are present at wavelengths between at a wavelength about 1535 $cm^{-1}$ which is related to the bending of N—H groups and stretching vibration of C—H groups.

The peaks of amide III are present at a wavelength of about 1237 cm$^{-1}$ due to an in-phase combination of C—N stretching and in-plane bending of N—H groups. Therefore, the intensified peaks at wavelengths between about 1500 cm$^{-1}$ about 1700 cm$^{-1}$ in the spectra of keratin 508, keratin-conjugated poloxamer 510, and nanocomposite 512 are attributed to the presence of the keratin as a fibrous protein which includes amino acid monomers.

Referring again to FIG. 5, after chemical crosslinking the keratin with the conjugated poloxamer by the genipin as the natural crosslinker, the location and intensity of characteristics peaks of amide type I and II are changed in the spectrum of keratin-conjugated poloxamer 510 in comparison with the spectrum of keratin 508. For example, the stretching vibration of C═O groups in the amide I band is shifted to lower wavelengths from about 1650 cm$^{-1}$ to about 1640 cm$^{-1}$ in the spectrum of keratin-conjugated poloxamer 510. Therefore, this observation may indicate the formation of secondary amide linkages as a result of crosslinking reactions between the primary amine groups of keratin and chitosan with the ester groups of genipin molecules. The interactions between the keratin and the conjugated poloxamer probably exist through hydrogen bonding between amine groups of chitosan and functional groups of keratin molecules.

Referring again to FIG. 5, after introducing layered silicate nanoparticles to the keratin-conjugated poloxamer, a new peak at a wavelength about 1000 cm$^{-1}$ appeared in the spectrum of nanocomposite 512 corresponding to the stretching vibration of the Si—O groups in the silicate nanoparticles. The stretching vibration of Si—OH groups of silicate nanoparticles overlaps with the stretching vibration of hydroxyl groups of the conjugated poloxamer at wavelengths between about 3400 cm$^{-1}$ about 3600 cm$^{-1}$.

According to the spectrum of the nanocomposite 512, hydrogen bonding between amine groups and carboxyl groups of the chitosan and the keratin with the oxygen-containing groups of the silicate nanoparticles is inevitable. Moreover, exfoliation of the silicate nanoparticles within the nanocomposite may induce physical crosslinking without affecting the chemical structure of the nanocomposite.

Example 4: Thermosensitive Behavior of the Hydrogel

A suitable injectable nanocomposite should be a liquid with low viscosity under non-physiological conditions to allow reproducible administration. After injection, it should undergo a rapid phase transition to form a strong hydrogel capable of withstanding shear forces at physiological conditions. In this example, the thermosensitive behavior of an exemplary hydrogel, which was fabricated as described accordingly to exemplary embodiments in the present disclosure, was studied.

The sol-gel transition temperature of the nanocomposite in phosphate buffered slain (PBS) was determined using a vial tilting method. At first, samples were incubated in a water bath and the temperature was gradually increased with an increment of about 1° C. At each temperature point, the samples were equilibrated for at least about 5 minutes. After that, the phase-transition temperature was determined after about 2 minutes when no fluidity was visually observed. The poloxamer copolymers showed a phase transition from sol to gel with increasing temperature up to about 25° C. However, the complete gelation of the poloxamer occurred at a temperature of about 32° C. The obtained hydrogels were transparent and showed a good consistency without any sliding or shifting when flipping the vials over.

Furthermore, it was found that the conjugated poloxamer with a concentration of at least about 17% of weight of the solid polymer in PBS was sufficient for the sol-gel transition. However, a higher concentration of poloxamer molecules, for example, about 20% was required to attain viscoelastic hydrogels upon increasing the temperature.

The thermo-reversible behavior of poloxamer was ascribed to the micelle formation at a temperature above the lower critical solution temperature (LCST) or at a concentration above the critical micelle concentration (CMC) as a result of poly (p-phenylene oxide) (PPO) block dehydration of the poloxamer molecules. The formation of highly ordered structures and micelle entanglements due to the hydrophobic interactions of the PPO groups and the dehydrated chitosan were proposed as a driving force in formation of the hydrogel. Grafting hydrophilic polymers such as chitosan onto the poloxamer copolymers increased the hydrophilicity of the hydrogel. Therefore, this may lead to an increase in the sol-gel temperature since the hydrophobic interactions are compensated at higher temperatures by enhanced polymer-water interactions.

Moreover, the sol-gel transition behavior of the conjugated poloxamer may be tuned during the crosslinking reactions of the conjugated poloxamer and the keratin with the genipin and after adding the plurality of the silicate nanoparticles to the keratin-conjugated poloxamer through the synergistic effects of these materials with the thermosensitive poloxamer. For instance, the gelation temperature of the crosslinked hydrogel in the presence of about 10 mM of genipin was about 37° C. Also, the higher hydrophobic PPO blocks adsorbed onto the charged surfaces of the silicate nanoparticles may provide a platform for a delayed gelation through the hydrophobic interactions of the PPO blocks. Therefore, addition of the silicate nanoparticles decreased the phase transition temperature and the required polymer concentration for the gelation. For example, incorporating 3% of silicate nanoparticles in the nanocomposite transforms the nanocomposite into the hydrogel at a temperature of about 35° C.

Example 5: Rheological Studies of the Hydrogel

It is important to study the rheological properties of the hydrogel under the physiological condition. In this example, rheological properties of an exemplary hydrogel, which was fabricated as described accordingly to exemplary embodiments in the present disclosure, were determined using oscillatory rheometry through measuring the storage modulus (G') and the loss modulus (G") versus temperature and angular frequency.

Figure 6A:
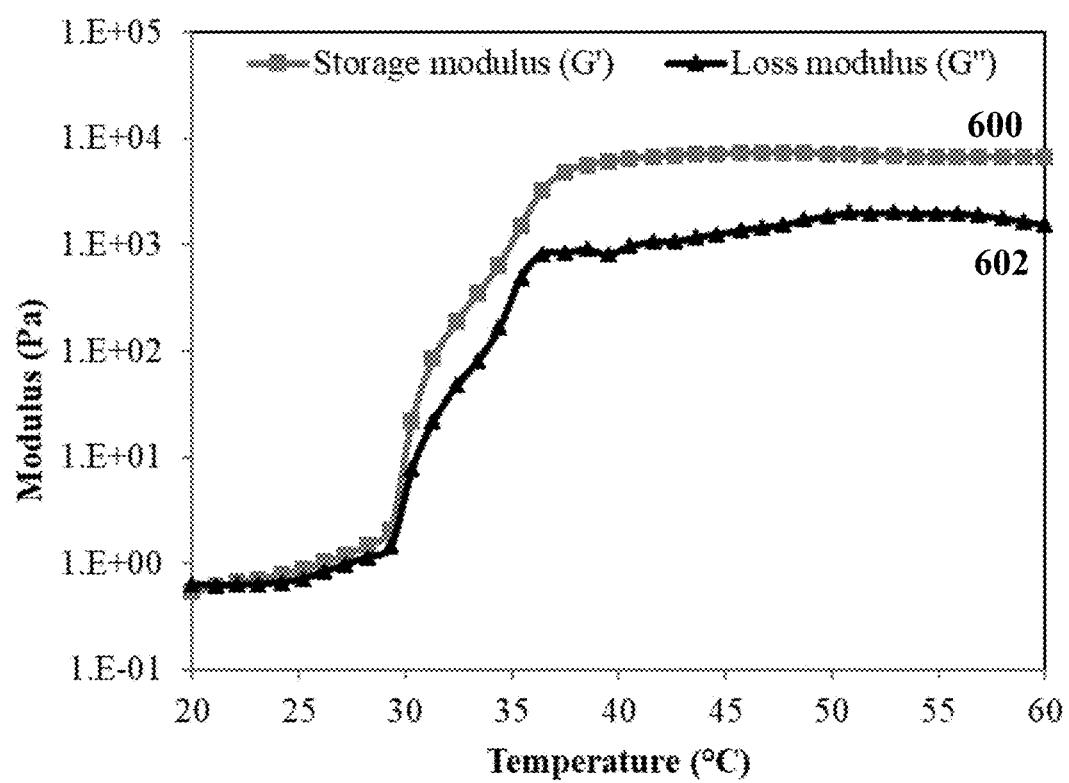
FIG. 6A illustrates storage modulus and loss modulus of an exemplary hydrogel at different temperatures, consistent with one or more exemplary embodiments of the present disclosure.

FIG. 6A shows a graph of storage modulus (G') 600 and loss modulus (G") 602 of an exemplary hydrogel at different temperatures and at an angular frequency of about 1 Hz, consistent with one or more exemplary embodiments of the present disclosure. Referring to FIG. 6A, the values of storage modulus (G') 600 and loss modulus (G") 602 were gradually increased as the temperature rises to about 30° C. At higher temperatures, the gelation process significantly increases storage modulus (G') 600 and loss modulus (G") 602. The higher growth rate of storage modulus (G') 600 compared to loss modulus (G") 602 indicates stiffening and the development of the hydrogel structure.

Figure 6B:
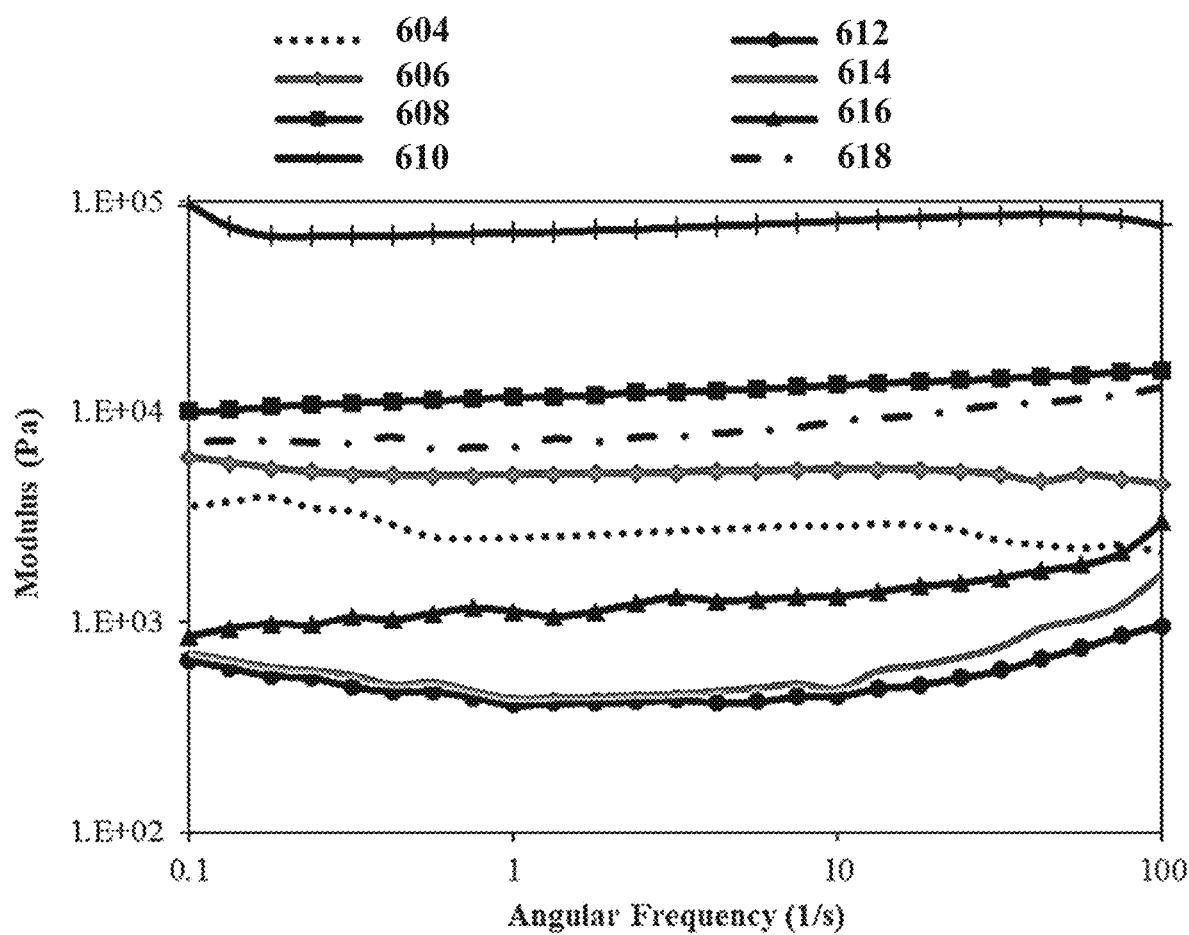
FIG. 6B illustrates storage modulus and loss modulus of an exemplary hydrogel at different angular frequencies, consistent with one or more exemplary embodiments of the present disclosure.

Frequency sweep experiments were also carried out to investigate the viscoelastic properties. FIG. 6B shows a graph of the storage modulus (G') and the loss modulus (G")

of different exemplary hydrogels at different angular frequencies and at a temperature of about 37° C., consistent with one or more exemplary embodiments of the present disclosure. The preformed hydrogels were subjected to oscillatory shear tests with a frequency sweep from about 0.1 Hz to about 100 Hz in the linear viscoelastic region.

The storage modulus (G') graphs of the FIG. 6B are as follows: G' of keratin-conjugated poloxamer without genipin 604, G' of keratin-conjugated poloxamer with 5 mM genipin 606, G' of keratin-conjugated poloxamer with 10 mM genipin 608, and G' of keratin-conjugated poloxamer with 10 mM genipin and 6% Laponite nanoparticles 610. The loss modulus (G") graphs of the FIG. 6B are as follows: G" of keratin-conjugated poloxamer without genipin 612, G" of keratin-conjugated poloxamer with 5 mM genipin 614, G" of keratin-conjugated poloxamer with 10 mM genipin 616, and G" of keratin-conjugated poloxamer with 10 mM genipin and 6% Laponite nanoparticles 618.

Referring to FIG. 6B, the graphs of storage modulus of exemplary hydrogels exhibit almost a frequency independent feature, which reveals the formation of stable crosslinked networks in the hydrogels. According to the graphs of the storage modulus (G') and the loss modulus (G"), it can be concluded that the strong modulus of the exemplary hydrogels is more than the loss modulus of them over the measured angular frequencies. Therefore, the exemplary hydrogels have a characteristic for a solid-like material with G' values more than G" values.

Referring again to FIG. 6B, the viscoelastic performance of the hydrogels is improved after crosslinking and addition of the Laponite nanoparticles. The interactions between the Laponite nanoparticles and the polymeric chains of chitosan affect the mechanical properties of the hydrogels. Moreover, the enhanced crosslinking density of the hydrogel by means of genipin, as well as the presence of exfoliated layers of Laponite nanoparticles, improves the shear moduli of the hydrogels.

Example 6: Swelling and Degradation Analysis of the Hydrogel

The swelling behavior of the hydrogel may affect their biological performance and mechanical properties as well as the diffusion rate of fluids. These properties may be generally influenced by many factors such as crosslinking density, gel composition, and porosity. In order to determine swelling ratio and in-vitro stability of an exemplary hydrogel, different exemplary hydrogels were incubated gently in PBS at a temperature of about 37° C. After predetermined time intervals, the supernatants were removed, and the swelling ratio of each hydrogel was determined after about 24 hours by the following formula:

$$SR(\%) = \frac{W_s - W_0}{W_0} \times 100,$$

$W_s$ stands for weight of the swollen hydrogel and $W_0$ stands for the initial weight of each hydrogel.

Figure 7A:
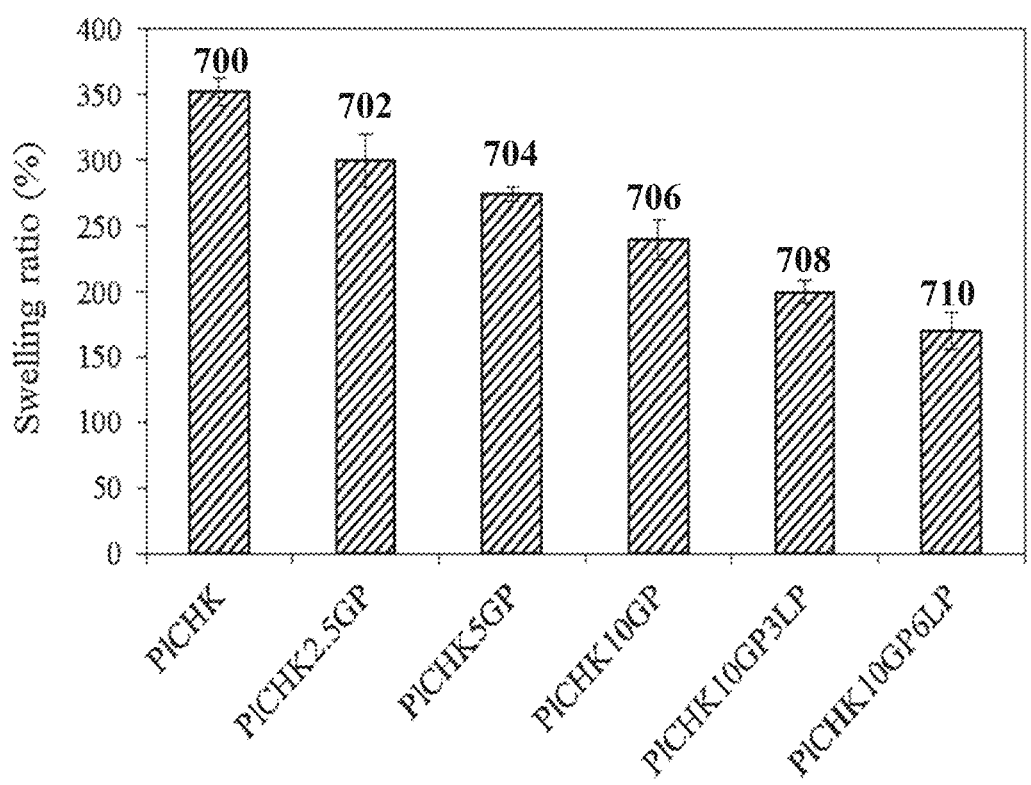
FIG. 7A illustrates the swelling ratio of different exemplary hydrogels, consistent with one or more exemplary embodiments of the present disclosure.

FIG. 7A shows the swelling ratios of different exemplary hydrogels, consistent with an exemplary embodiment of the present disclosure. The swelling ratios shown in FIG. 7A are related to keratin-conjugated poloxamer (PLCHK) 700, keratin-conjugated poloxamer containing 2.5 mM genipin (PLCHK2.5GP) 702, keratin-conjugated poloxamer containing 5 mM genipin (PLCHK5GP) 704, keratin-conjugated poloxamer containing 10 mM genipin (PLCHK10GP) 706, keratin-conjugated poloxamer containing 10 mM genipin and 3% Laponite nanoparticles (PLCHK10GP3LP) 708, and keratin-conjugated poloxamer containing 10 mM genipin and 6% Laponite nanoparticles (PLCHK10GP6LP) 710.

Referring to FIG. 7A, the exemplary hydrogels display significant water absorption capability owing to their hydrophilic nature and highly porous structure. According to the swelling ratios, it can be concluded that crosslinking the keratin-conjugated poloxamer with genipin and adding the Laponite nanoparticles to the keratin-conjugated poloxamer decrease the swelling ratio of the hydrogels. Crosslinking the keratin-conjugated poloxamer with genipin decrease the water adsorption capacity of the exemplary hydrogels because the hydrophilic groups is consumed in the crosslinking reactions. Moreover, adding the Laponite nanoparticles to the keratin-conjugated poloxamer decrease the pore size of the hydrogels; therefore, the water adsorption capacity of the exemplary hydrogels is decreased.

Due to the long repair time of cartilage, it is crucial that the engineered scaffolds could maintain a durable ECM-like structure under physiological environment until tissue regeneration. Mass erosion and degradation rates of the exemplary hydrogels were also determined at different time intervals up to about 30 days.

Figure 7B:
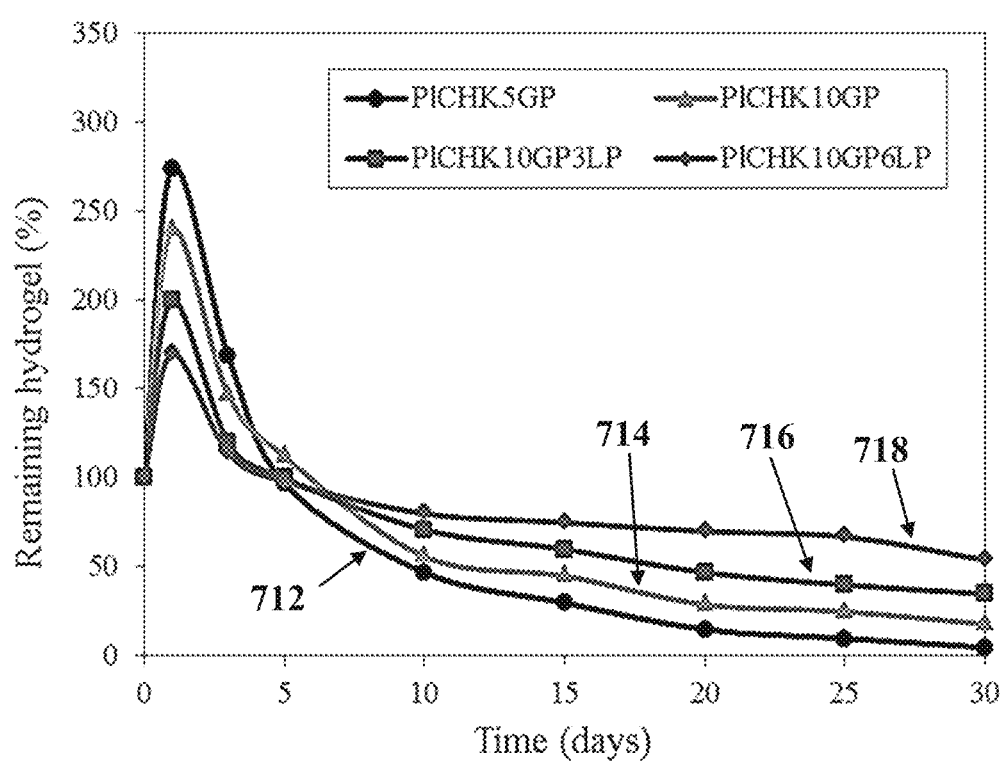
FIG. 7B illustrates degradation profile of different exemplary hydrogels, consistent with one or more exemplary embodiments of the present disclosure.

FIG. 7B shows degradation profile of different exemplary hydrogels for the percentage of remaining hydrogels after different incubation times in PBS, consistent with one or more exemplary embodiments of the present disclosure. The exemplary hydrogels are keratin-conjugated poloxamer containing 5 mM genipin (PLCHK5GP) 712, keratin-conjugated poloxamer containing 10 mM genipin (PLCHK10GP) 714, keratin-conjugated poloxamer containing 10 mM genipin and 3% Laponite nanoparticles 716, keratin-conjugated poloxamer containing 10 mM genipin and 6% Laponite nanoparticles 718.

Referring to FIG. 7B, the initial rise in the percentage of the remaining hydrogels is attributed to the water uptake and swelling of the hydrogels. It was found that degradation of the hydrogels was significantly retarded by crosslinking because of the more compact and stable structures in the crosslinked form of the hydrogels. The crosslinked form of the hydrogels has intramolecular and intermolecular networks which hinders the degradation of the hydrogels via dissolution of the hydrophilic polymeric chains into the aqueous phase.

Referring again to FIG. 7B, the hydrogels containing Laponite nanoparticles was the most stable hydrogels among different exemplary hydrogels. The presence of Laponite nanoparticles as the charged silicate nanoparticles could interact with the molecules of poloxamer as an effective physical crosslinker in the structure of the exemplary hydrogels. On the other hand, the presence of genipin as the chemical crosslinker improved the stability of hydrogels under the physiological environment. Therefore, the combined physicochemical crosslinked structure of the hydrogels caused long-term stability of the hydrogels, which is about more than 30 days.

Example 7: Cytotoxicity Analysis of the Hydrogel

Ideal scaffolds for tissue engineering may be biodegradable with a favorable microenvironment for cell adhesion to promote tissue regeneration. In this example, cytotoxicity of different exemplary hydrogels, which was fabricated as described according to exemplary embodiments in the present disclosure, was studied through the 3-(4,5-dimethylthiazol-2-yl)-2,5 diphenyltetrazolium bromide (MTT) assay using articular chondrocytes. The articular chondrocytes were isolated from knee joints of New Zealand white rabbits according to the ethical committee of national cell bank of Iran.

Figure 8:
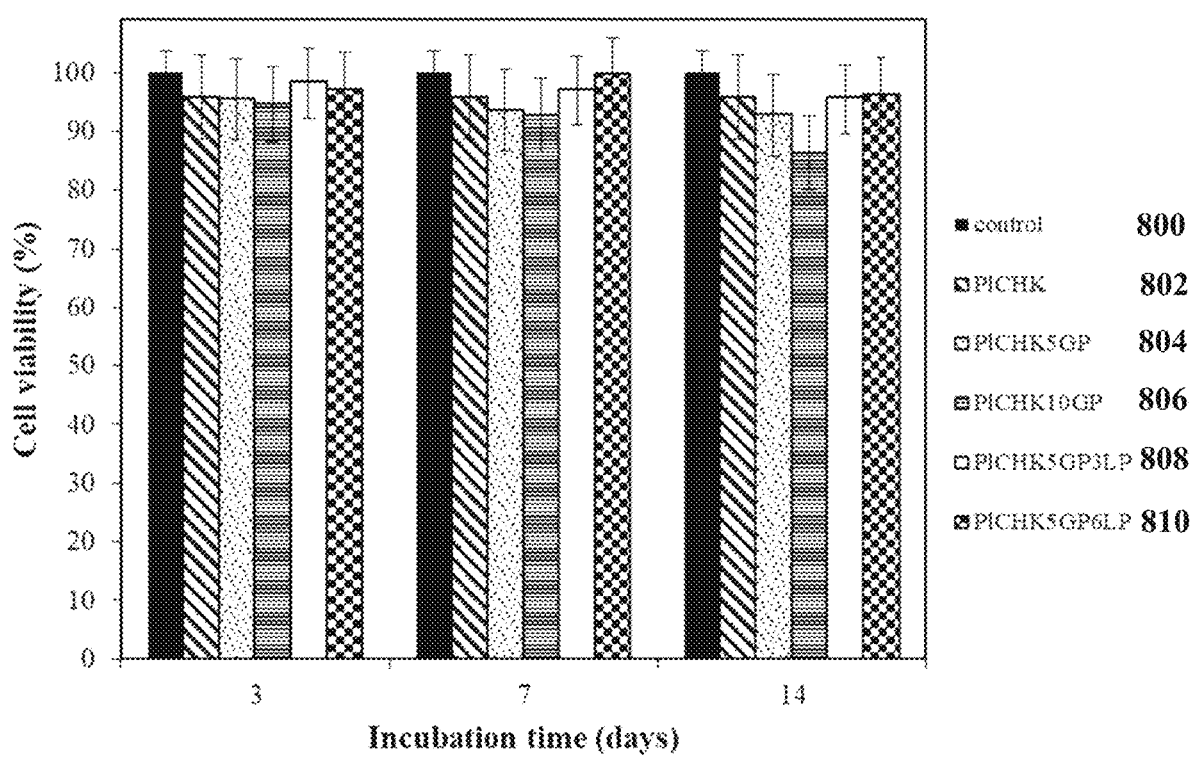
FIG. 8 illustrates cell viability of the articular chondrocytes in a cytotoxicity assay of an exemplary hydrogel, consistent with one or more exemplary embodiments of the present disclosure.

FIG. 8 shows cell viability of the articular chondrocytes at different time after incubating the articular chondrocytes with different exemplary hydrogels, consistent with one or more exemplary embodiments of the present disclosure. The groups of the MTT assay were control group 800, keratin-conjugated poloxamer (PLCHK) 802, keratin-conjugated poloxamer containing 5 mM of genipin (PLCHK5GP) 804, keratin-conjugated poloxamer containing 10 mM of genipin (PLCHK10GP) 806, keratin-conjugated poloxamer containing 5 mM of genipin and 3% of Laponite nanoparticles (PLCHK5GP3LP) 808, keratin-conjugated poloxamer containing 5 mM of genipin and 6% of Laponite nanoparticles (PLCHK5GP6LP) 810.

Referring to FIG. 8, the viability of articular chondrocytes after 14 days of incubation on the exemplary hydrogel was about 85% compared to the control group. This observation reflects the biocompatibility of the exemplary hydrogels and confirms the nontoxicity of the genipin in the structure of hydrogels. Genipin is a plant extracted crosslinker with anti-inflammatory, anti-fibrotic, neurogenic, and hemostatic properties.

The experimental results have also shown that the nanocomposite hydrogels exhibit slightly higher cytocompatibility than the polymeric hydrogels because dissolution of the biocompatible silicate nanoparticles and inorganic ions such as sodium ($Na^+$), Ortho-silicic acid ($Si(OH)_4$), magnesium ($Mg^{2+}$), and lithium ($Li^+$) in the physiological solution may improve cellular viability. Particularly, divalent cations such as magnesium Mg') play significant roles in cellular adhesion to biomaterial surfaces.

Moreover, Ortho-silicic acid ($Si(OH)_4$) has been shown to stimulate collagen formation and osteoblastic differentiation. The surface chemistry, hydrophilicity and porous structure of hydrogels may influence their biocompatibility, attachment, and migration of cells. It was shown herein that incorporation of biocompatible layered silicate nanoparticles in the hydrogels may enhance cell adhesion and proliferation as a viable strategy to maintain chondrogenic induction.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in the light of the attached claims and their equivalents. Also, various modifications and changes may be made within the scope of the attached claims.

What is claimed is:

1. A method for cartilage tissue engineering, comprising:
   fabricating a nanocomposite, comprising:
       forming an activated poloxamer by carboxylating a poloxamer;

forming a conjugated poloxamer by grafting the activated poloxamer to chitosan;

forming a keratin-conjugated poloxamer by crosslinking keratin with the conjugated poloxamer using genipin with a concentration between 1 mM and 10 mM; and forming the nanocomposite by adding a plurality of layered silicate nanoparticles with a weight percent of 3%, or 6% of the total weight of the nanocomposite to the keratin-conjugated poloxamer;

injecting the nanocomposite into a defect site of cartilage; and forming a hydrogel in the defect site of the cartilage using a sol-gel transition responsive to increasing temperature of the nanocomposite from room temperature to 37° C.

2. The method according to claim 1, wherein grafting the activated poloxamer to the chitosan comprises:

forming a first solution by dissolving the activated poloxamer in a phosphate buffer solution with a pH between 5 and 5.5;

forming a second solution by adding 1 ethyl-3-(3-dimethylaminopropyl) carbodiimide (EDC) and N-hydroxysuccinimide (NHS) to the first solution; and forming a third solution by adding a chitosan solution to the second solution, the third solution comprising the conjugated poloxamer.

3. The method according to claim 1, wherein grafting the activated poloxamer to the chitosan comprises grafting the activated poloxamer to the chitosan with a weight ratio between 8:1 and 12:1.

4. The method according to claim 1, wherein crosslinking the keratin with the conjugated poloxamer comprises:

forming a mixture by adding the keratin to the conjugated poloxamer, and adding the genipin to the mixture.

5. The method according to claim 4, wherein adding the keratin to the conjugated poloxamer comprises adding the keratin to the conjugated poloxamer with a weight ratio between 1:8 and 1:12.

6. The method according to claim 4, wherein adding the genipin to the mixture comprises adding a genipin solution with a concentration between 1 mM and 10 mM to the mixture.

7. The method according to claim 1, wherein the hydrogel has a porous structure with a pore size between 5 μm and 100 μm.

8. The method according to claim 1, wherein the hydrogel has a swelling ratio between 175% and 250%.

* * * * *